United States Patent [19]

Foglio et al.

[11] 4,143,037
[45] Mar. 6, 1979

[54] THIOHYDRAZOAZETIDINONES

[75] Inventors: Maurizio Foglio; Giovanni Franceschi; Paolo Masi; Antonino Suarato, all of Milan, Italy

[73] Assignee: Societa' Farmaceutici Italia S.p.A., Milan, Italy

[21] Appl. No.: 797,608

[22] Filed: May 16, 1977

Related U.S. Application Data

[62] Division of Ser. No. 735,973, Oct. 27, 1976, abandoned, which is a division of Ser. No. 586,376, Jun. 12, 1975, Pat. No. 4,012,381.

[30] Foreign Application Priority Data

Jun. 12, 1974 [IT] Italy .................. 23887 A/74

[51] Int. Cl.$^2$ .......................................... C07D 205/08
[52] U.S. Cl. ............................................. 260/239 A
[58] Field of Search ................. 260/239 A, 599, 666

[56] References Cited
U.S. PATENT DOCUMENTS 4,036,835  7/1977  Foglio et al. ................ 260/243 C

OTHER PUBLICATIONS

Linke et al., Chem. Abs. 74, 64123c (1971).

*Primary Examiner*—Mark L. Berch
*Attorney, Agent, or Firm*—Stevens, Davis, Miller & Mosher

[57] ABSTRACT

A process is disclosed for preparing compounds of structure:

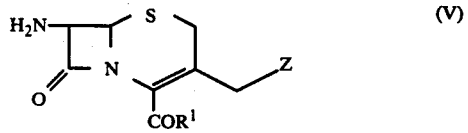

where $R^1$ is hydroxyl, alkoxy with 1 to 4 carbon atoms, trichloroethoxy, benzyloxy, p-methoxybenzyloxy, p-nitrobenzyloxy, benzhydryloxy, triphenylmethoxy, phenacyloxy, or p-halophenacyloxy;

Z is hydrogen, hydroxyl, —O-alkyl, —O—CO-alkyl, —Br, —I, —N$_3$, —O—CO—CH$_3$, O—CO—NH$_2$, or an S-mononuclear heterocyclic ring, starting from

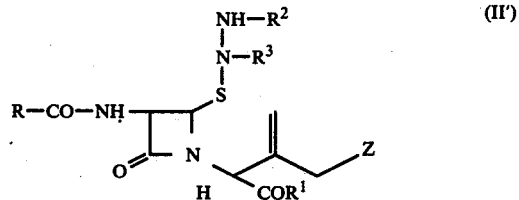

where R is hydrogen, alkyl having from 1 to 4 carbon atoms, cyano-methyl, thienyl-methyl, furyl-methyl, naphthyl-methyl, phenyl-methyl, phenoxy-methyl, phenyl-isopropyl, phenoxy-isopropyl, pyridyl-4-thiomethyl, or tetrazolyl-1-methyl;

$R^2$ and $R^3$ are lower alkyl, a mononuclear aryl ring, CN, a mononuclear heterocyclic ring or the radicals —COR$^4$, —COOR$^4$,

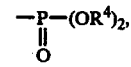

—CONHR$^4$, or $R_2$ and $R_3$ together represent

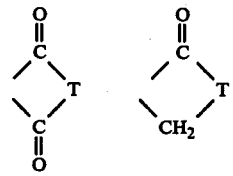

where T represents

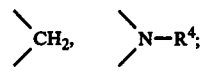

and R$^4$ is a lower alkyl, a mononuclear aryl or heterocyclic ring, wherein the compound (II') is reacted with a phosphorous halide in the presence of a tertiary amine, the corresponding imino chloride is reacted with a lower aliphatic alcohol, the iminoether so formed is hydrolyzed in an acid medium, and the resultant 3-amino-2-β-thiohydrazoazetidinone:

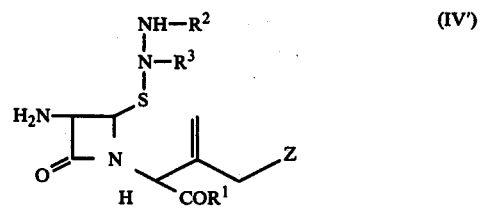

in which $R^1$, $R^2$, $R^3$ and Z have the meanings given heretofore, is reacted between $-100°$ and $+120°$ C. with inorganic basic or weakly acid oxides or inorganic and organic bases, to give (V).

5 Claims, No Drawing

THIOHYDRAZOAZETIDINONES

This is a division of application Ser. No. 735,973 filed Oct. 27, 1976, now abandoned which in turn is a division of application Ser. No. 586,376, filed June 12, 1975, now U.S. Pat. No. 4,012,381.

The present invention relates to a process for preparing cephalosporins and intermediates.

More particularly, the invention relates to a new process for preparing derivatives of 7-amino-cephalosporanic acid (7-ACA), of 7-aminodesacetoxy-cephalosporanic acid (7-ADCA), and of 3-amino-2-thiohydrazoazetidinones as intermediates.

U.S. Pat. No. 4,036,835, issued July 19, 1977, describes, amongst other things, 3-acylamino-2β-thiohydrazoazetidinones of structure:

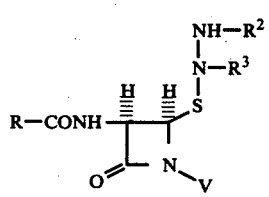

where V may be hydrogen, or an aliphatic, aromatic, arylaliphatic or acylic residue, and in particular the residues:

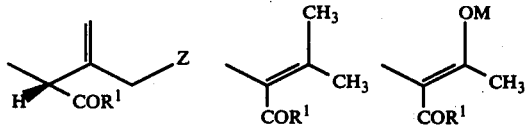

where R is selected from the class consisting of hydrogen, alkyl having from 1 to 4 carbon atoms, cyanomethyl, thienyl-methyl, furyl-methyl, naphthyl-methyl, phenyl-methyl, phenoxy-methyl, phenyl-isopropyl, phenoxy-isopropyl, pyridyl-4-thiomethyl, and tetrazolyl-1-methyl; M is hydrogen or lower alkyl.

$R^1$ is selected from the class consisting of hydroxyl, alkoxy with 1 to 4 carbon atoms, trichloro-ethoxy, benzyloxy, p-methoxybenzyloxy, p-nitrobenzyloxy, benzhydryloxy, triphenylmethoxy, phenacyloxy, and p-halophenacyloxy;

Z is selected from the class consisting of hydrogen, hydroxyl, —O-alkyl, —O—CO-alkyl, —Br, —I, —N$_3$, —NH$_2$, —O—CO—CH$_3$, O—CO—NH$_2$, and an S-mononuclear nitrogen heterocyclic ring;

$R^2$ and $R^3$ are equal or different and represent a lower alkyl, a mononuclear aryl ring, CN, a mononuclear heterocyclic ring or the radicals —COR$^4$, —COOR$^4$,

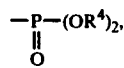

—CONHR$^4$;

or R$^2$ and R$^3$ together may represent the residues:

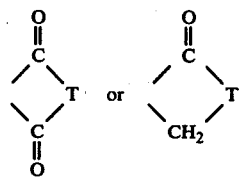

where T represents CH$_2$,

and R$^4$ is a lower alkyl, a mononuclear aryl ring or a mononuclear heterocyclic ring.

It has now surprisingly been found — and this constitutes one of the principal objects of the present invention — that said 3-acylamino-2β-thiohydrazoazetidinones (II) may be deacylated to the correspondingly 3-amino-2β-thiohydrazetidinones (IV) by successive treatment with a halogenating agent, a lower aliphatic alcohol and a hydrolyzing agent in accordance with the equation:

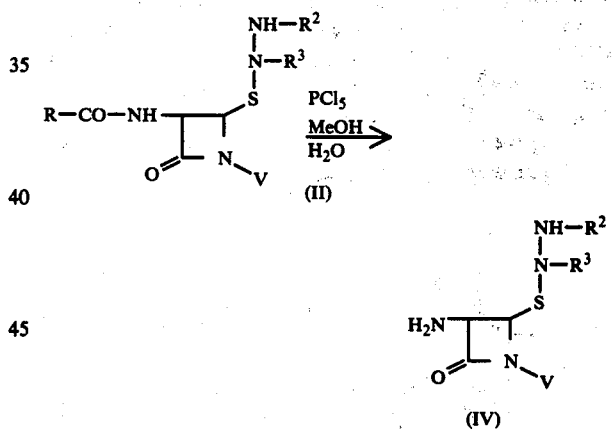

where R, R$^2$, R$^3$ and V have the meanings given above.

It has also surprisingly been found that if the said 3-amino-2β-thiohydrazoazetidinones, in which the substituent V represents the residue

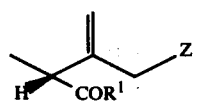

are reacted with inorganic oxides or bases, as described in aforesaid U.S. Pat. No. 4,036,835, they cyclize to derivatives of 7-ACA or 7-ACDA in accordance with the equation:

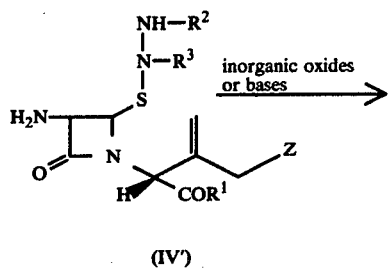

(IV')

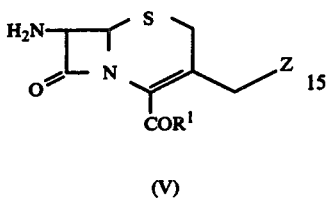

(V)

where $R^1$, $R^2$, $R^3$ and Z have the meanings given above.

This process, the details of which will be described hereinafter, represents a new and surprising method for preparing derivatives of 7-amino-cephalosporanic acid (7-ACA) and of 7-amino-desacetoxycephalosporanic acid (7-ADCA), which are key intermediates for the preparation of a very wide series of cephalosporins.

A further object of the present invention is the preparation of cephalosporins of structure (III), starting from the aforementioned compounds of structure (IV'), by reacting the latter with an R—CO—X' compound to give, in a first stage, 3-acylamino-2β-thiohydrazoazetidinones of structure (II'), which when then reacted with inorganic oxides or bases in accordance with the conditions described in U.S. Pat. No. 4,036,835 finally give the cephalosporins of structure (III) in accordance with the equations:

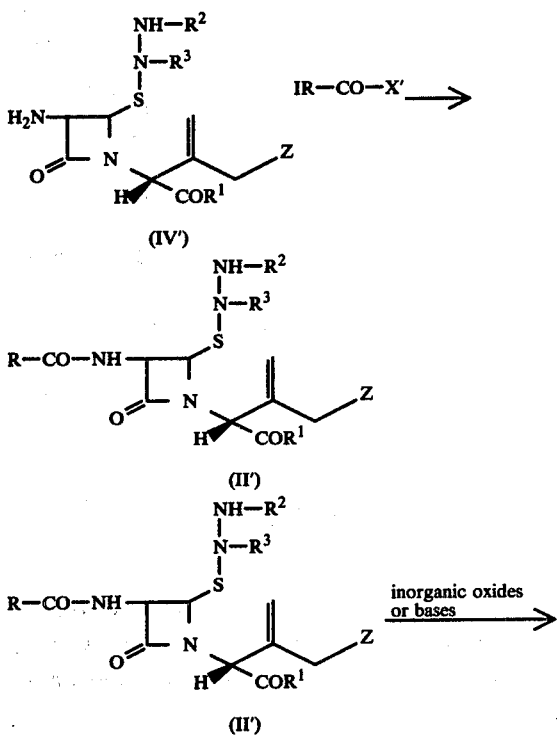

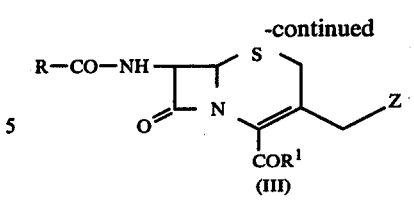

(III)

where R, $R^1$, $R^2$, $R^3$ and Z have the meanings given above, and X' represents chlorine, bromine, hydroxyl, an acyloxy radical with 1 to 4 carbon atoms, or the residue

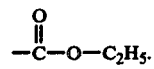

In the first step of the process according to the present invention, the 3-acylamino-2β-thiohydrazoazetidinone is converted into an imino-halide by reaction with a phosphorous halide such as phosphorus pentachloride in a suitable solvent (e.g., benzene) at a temperature between −10° C. and +100° C. in the presence of a tertiary amine such as pyridine. After evaporating the solvent under vacuum, the residue is redissolved at 0° C. in a lower aliphatic alcohol, preferably methanol, and left for some hours at room temperature. In this way the corresponding imino-ether is formed. The solvent is eliminated by evaporating to dryness and the residue is redissolved in an aqueous solvent such as tetrahydrofuran/water to hydrolyze the imino-ether to the amine (IV').

The reaction product is left at room temperature, then the solvent is evaporated under vacuum; water, sodium chloride and a solvent immiscible with water (e.g., ethyl acetate) are added and the mixture shaken.

The desired product (IV') passes entirely into the aqueous layer, from which it is extracted by slight alkalization and extracting thoroughly with the solvent immiscible with water.

The cyclizing of the intermediate (IV') to derivatives of 7-ACA or 7-ADCA (V) constitutes, as stated heretofore, a new and surprising method for the practical preparation of 7-amino-cephalosporanic acid and 7-amino-desacetoxy-cephalosporanic acid.

The intermediate compound (IV') is reacted in a suitable solvent (e.g., benzene) at a temperature between −100° C. and +120° C. with inorganic oxides such as $Al_2O_3$, $Fe_2O_3$, $Cr_2O_3$, $SiO_2$, or with inorganic or organic bases such as KOH, $Na_2CO_3$, $NH_4OH$, alkali metal alcoholates, aliphatic, aromatic and heterocyclic amines, alkylammonium bases and basic resins. In this way, the derivative (V) is obtained, which is thereupon isolated and purified in per se known manner.

The present invention also relates to a modification of the process for preparing cephalosporins of structure (III) described in aforesaid U.S. Pat. No. 4,036,835

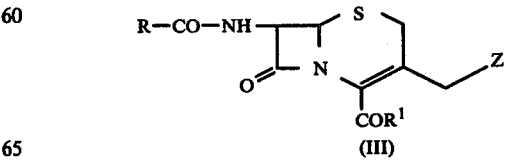

(III)

starting from a 3-amino-2β-thiohydrazoazetidinone of structure (IV') described heretofore. This is acylated on the amine group in position 3 by reaction with a compound R—CO—X' to give 3-acylamino-2β-thiohydrazoazetidinones of structure (II'). These intermediates, as described and claimed in the aforementioned U.S. Pat. No. 4,036,835, are finally cyclized according to the same process as described above, i.e., by treating with inorganic oxides or bases, to give finally the cephalosporins of the said structure (III), where R, R¹, X' and Z have the meanings given above.

The following examples serve to illustrate the invention without however limiting it:

EXAMPLE 1

Methyl-2β-thiohydrazodicarboxyethyl-α-isopropenyl-4-oxo-3β-amino-1-azetidine acetate.

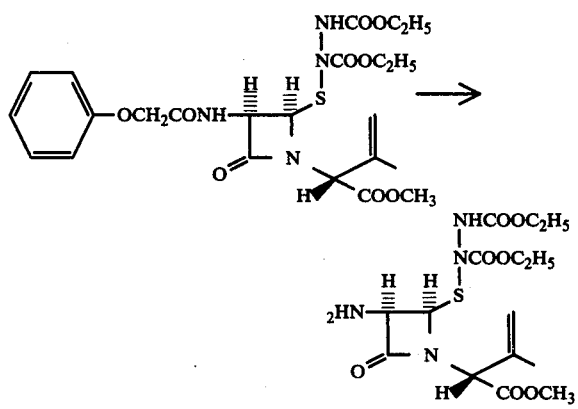

1.05 g of PCl₅ are added to a solution of 2.2 g of methyl-2β-thiohydrazodicarboxyethyl-α-isopropenyl-4-oxo-3β-phenoxyacetamido-1-azetidine acetate in 100 ml of anhydrous benzene containing 1.5 ml of anhydrous pyridine, and the whole is heated to 50° C. for 60 minutes. The solvent is evaporated and the residue, cooled to 0° C., is redissolved in cold methanol, and left at room temperature for 2 hours. The solvent is evaporated and the residue redissolved, under cooling, in tetrahydrofuran/water (1:1, v/v), after which it is left for 30 minutes at room temperature. The tetrahydrofuran is evaporated under vacuum, whereupon salt water and ethyl acetate are added and stirring applied.

The product passes entirely into the aqueous phase, from which it is extracted by alkalizing with NaHCO₃ and extracting several times with ethyl acetate. In this way, 1.1 g of the desired product are obtained.

I.R. (CH₂Cl₂): 3400 cm⁻¹ (NH and NH₂); 1760 cm⁻¹ (C=O βlactam); 1735 cm⁻¹ (C=O ester and carbamates).

EXAMPLE 2

Methyl-2β-thiohydrazodicarboxyethyl-α-isopropylidene-4-oxo-3β-amino-1-azetidine acetate.

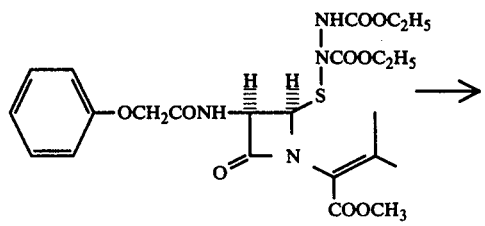

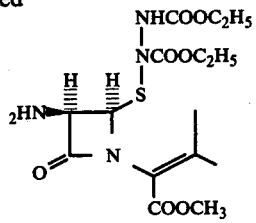

2.3 g of phosphorus pentachloride are added to a solution of 5.0 g of methyl-2β-thiohydrazodicarboxyethyl-α-isopropylidene-4-oxo-3β-phenoxyacetamido-1-azetidine acetate in 250 ml of anhydrous benzene containing 3 ml of anhydrous pyridine, and the mixture heated for 90 minutes at 50° C. The benzene is evaporated, and anhydrous methanol is added at 0° C., after which the mixture is left at room temperature for a further 90 minutes. The methanol is evaporated and a tetrahydrofuran/water mixture (1:1, v/v) is added under continuous cooling. It is left for a further 40 minutes at room temperature, the tetrahydrofuran is evaporated under vacuum, and salt water and ethyl acetate are added.

The product remains in the aqueous phase, which is alkalized with NaHCO₃ and repeatedly extracted with ethyl acetate. In this way 3.0 g of the desired product are obtained.

I.R. (CH₂Cl₂): 3400 cm⁻¹ (NH); 1755 cm⁻¹ (C=O βlactam); 1725 cm⁻¹ (C=O ester and carbamates).

EXAMPLE 3

2',2',2'-trichloroethyl-2β-thiohydrazodicarboxyethyl-α-isopropenyl-4-oxo-3β-amino-1-azetidine acetate.

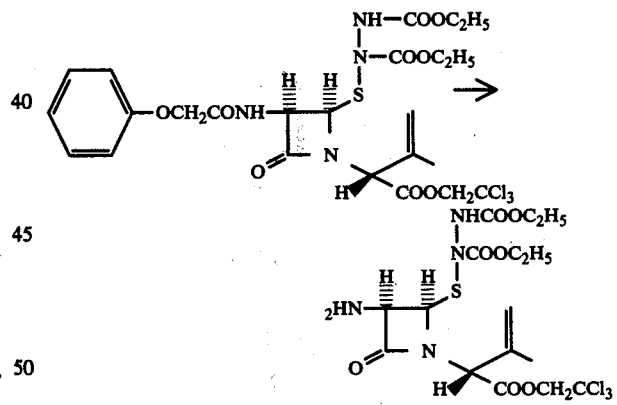

3 ml of anhydrous pyridine and 2.5 g of PCl₅ are added to a solution of 6.55 g of 2',2',2'-trichloroethyl-2β-thiohydrazodicarboxylethyl-α-isopropenyl-4-oxo-3β-phenoxyacetamido-1-azetidine acetate in 200 ml of anhydrous benzene, and the mixture is heated to 50° C. for 90 minutes. The benzene is evaporated and anhydrous methanol is added on cooling, after which it is left at room temperature for 60 minutes. The solvent is again evaporated and the residue dissolved, after cooling, in a tetrahydrofuran/water mixture (1:1, v/v). It is left for a further 30 minutes at room temperature, the tetrahydrofuran is evaporated, and salt water and ethyl acetate are added.

The aqueous phase is separated, alkalized with NaHCO₃ and extracted several times with ethyl acetate to give 3.7 g of the desired product.

I.R. (CH$_2$Cl$_2$): 3400 cm$^{-1}$ (NH and NH$_2$); 1760 cm$^{-1}$ (C=O β-lactam); 1735 cm$^{-1}$ (C=O ester and carbamates).

EXAMPLE 4

Methylester of 7-amino desacetoxycephalosporanic acid.

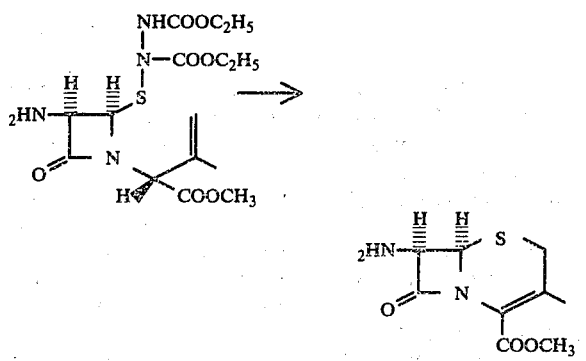

A 30% solution of KOH in water is added, under agitation in a magnetic stirrer, to a solution of 2 g of methyl-2β-thiohydrazodicarboxyethyl-α-isopropenyl-4-oxo-3β-amino-1-azetidine acetate in 100 ml of benzene, and the whole left at room temperature for 60 minutes. The organic layer is separated and washed several times with water. The product is chromatographed over silica with benzene-ethyl acetate.

In this way 0.800 g of product are obtained. m.p. 123°–124° C. (ethyl ether). The product thus obtained has chemical and physical characteristics (m.p., I.R., N.M.R., mass spectrum) equal to those of a sample prepared in another manner.

EXAMPLE 5

2',2',2'-trichloroethylester of 7-aminodesacetoxycephalosporanic acid

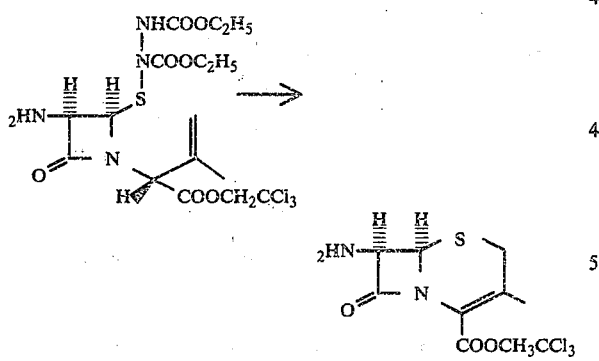

A 30% solution of KOH in water is added to a solution of 2.1 g of 2',2',2'-trichloroethyl-2β-thiohydrazodicarboxyethyl-α-isopropenyl-4-oxo-3β-amino-1-azetidine acetate in 100 ml of benzene, and the mixture kept under stirring for 60 minutes. The organic layer is separated and stirred with acidified water, thus causing the product to pass into the water as salt. The organic layer is eliminated, after which the aqueous layer is alkalized with NaHCO$_3$ and then extracted with ethyl acetate.

In this way, 1.3 g of the desired product are obtained. This product coincides with the characteristics reported in the literature (J. Org. Chem. 1971, 36, 1259). Furthermore, when treated in accordance with known methods, it gave 7-amino-desacetoxycephalosporanic acid (7-ADCA).

EXAMPLE 6

Methyl-2β-thiohydrazodicarboxyethyl-α-isopropylidene-4-oxo-3β-phenylacetamido-1-azetidine acetate

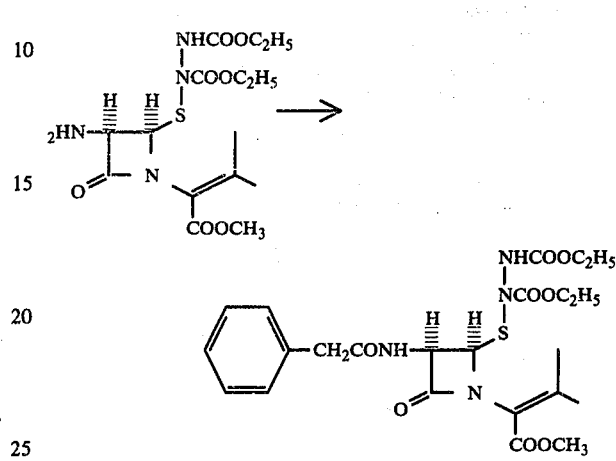

A solution of 2.0 g of methyl-2β-thiohydrazodicarboxyethyl-α-isopropylidene-4-oxo-3β-amino-1-azetidine acetate in 80 ml of benzene is combined, under stirring, with 40 ml of a saturated solution of NaHCO$_3$, and to this are added 1.5 ml of phenylacetyl chloride at 0° C. It is kept under stirring at room temperature for 60 minutes, and then the organic layer is separated, dried over Na$_2$SO$_4$, and evaporated. The residue is chromatographed over silica, eluting with benzene-ethyl acetate (70:30, v/v).

In this way, 2.1 g of the desired product are obtained.

IR (CHCl$_3$): 3420 cm$^{-1}$ (N—H); 1765 cm$^{-1}$ (C=O β-lactam); 1725 cm$^{-1}$ (C=O ester and carbamates); 1670 cm$^{-1}$ (C=O amide).

NMR (CDCl$_3$): 1.14 and 1.17 (two t, 6H, 2 CH$_3$—C(H$_2$)—), 2.02 and 2.19 (two s, 6 H,

2 CH$_3$—C=), 3.57 (s, 2 H, C$_6$(H$_5$)—CH$_2$—CO—), 3.67 (s, 3 H, COOCH$_3$), 4.08 (q, 4H, 2 CH$_2$—C(H$_3$) ), 4.88 (dd, 1 H, C(3)H), 5.70 (d, 1 H, C(4)H) and 6.5–7.4 δ (m, 7 H, 2 CONH and C$_6$H$_5$).

EXAMPLE 7

Methyl-2β-thiohydrazodicarboxyethyl-α-isopropenyl-4-oxo-3β-phenylacetamido-1-azetidine acetate

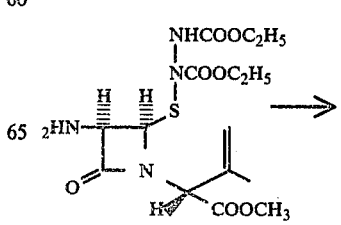

-continued

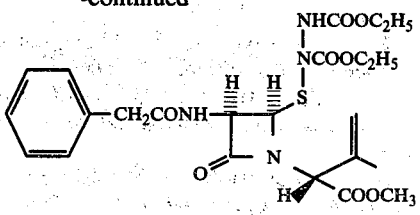

This is prepared in a like manner as the product of Example 6. The product obtained, when treated with bases in accordance with known manner, gave the corresponding desacetoxycephalosporin having characteristics equal to a sample prepared in another manner, as well as corresponding to the data reported in the literature. (J. Chem. Soc., 1971, 3540).

EXAMPLE 8

2′,2′,2′-trichloroethyl-2β-thiohydrazodicarboxyethyl-α-isopropenyl-4-oxo-3β-[N-(ter-butoxycarbonyl)-D-α-phenylglycinamido]-1-azetidine acetate

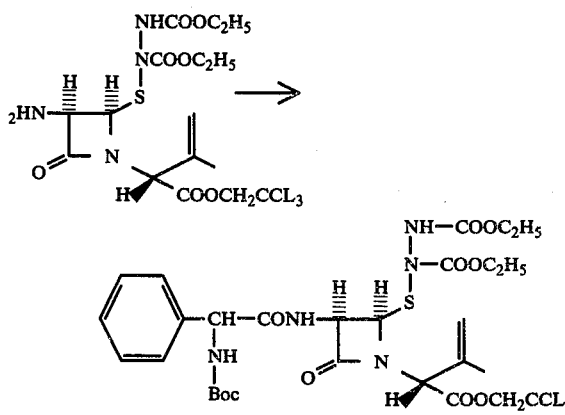

A solution of 1.1 g of carboterbutoxyphenylglycine and 0.62 m of triethylamine in 10 ml of methylene chloride are added at −15° C., under stirring, to 0.4 ml of ethylchloroformate dissolved in 10 ml of anhydrous methylene chloride. It is left for 30 minutes under these conditions. At this point a solution of 1.7 g of 2′,2′,2′-trichloroethyl-2β-thiohydrazodicarboxyethyl-α-isopropenyl-4-oxo-3β-amino-1-azetidine acetate in 30 ml of CH$_2$Cl$_2$ is added slowly, under stirring. The mixture is left for 3 hours at −10° C., whereupon water and CH$_2$Cl$_2$ are added. The organic layer is separated, the aqueous layer is again extracted with CH$_2$Cl$_2$, and the organic layers are dried and evaporated to give a residue which is chromatographed over silica with benzene-ethyl acetate (80:20, v/v) to give 2.1 g of the desired product.

NMR (DCDl$_3$): 1.14 and 1.17 (two t, 6 H, 2 CH$_3$—C(H$_2$)), 1.40 (s, 9 H, —C(CH$_3$)$_3$), 1.94 (s, 3 H, CH$_3$—C=), 4.08 (q, 4H, 2 CH$_2$—C(H$_3$)), 4.90 (s, 1 H,

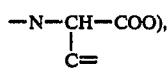

4.88 and 5.00 (2 d, 2 H, —COO—CH$_2$—CCl$_3$) 5.07 and 5.16 (widened s, 2 H, = CH$_2$), 5.28 (s, 1 H, $C_6(H_5)-CH-C-$,
    |
    N—

5,3–5.7 (m, 2 H, H of β-lactam) and 6.5–8.0 δ (m, 8 H; aromatic H and 3 NH).

EXAMPLE 9

2′,2′,2′-trichloroethyl-7-[N-(ter-butoxycarbonyl)-D-a-phenyl glycinamido]-3-methyl-3-cephem-4-carboxylate.

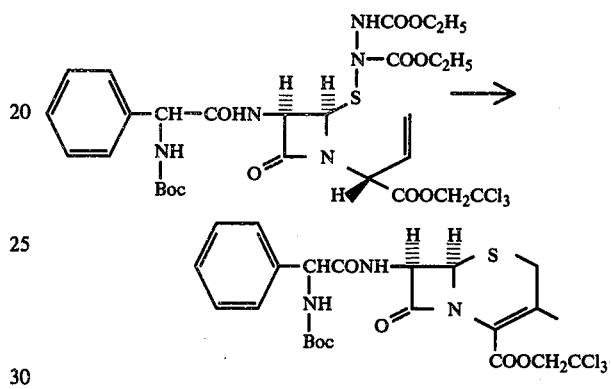

A solution of 0.4 g of 2′,2′,2′-trichloroethyl-2β-thiohydrazodicarboxyethyl-α-isopropenyl-4-oxo-3β-[N-(ter-butoxycarbonyl)-D-α-phenylglycinamide]-1-azetidine acetate in 100 ml of benzene is kept under stirring in the presence of an excess of Al$_2$O$_3$. The mixture is left in this condition for 2 hours, after which the Al$_2$O$_3$ is filtered off and the residue is chromatographed over silica, eluting with benzene-ethyl acetate (90:10, v/v), to give 200 mg of the desired cephalosporanic product.

This product has the characteristics reported in the literature (J. Org. Chem. 1971, 36, 1259), and when treated in accordance with known methods, gave 7-(D-amino-α-phenylacetamido)-3-methyl-3-cephem-4-carboxylic acid, with the same characteristics as reported in the literature (J. Org. Chem. 1971, 36, 1259).

What is claimed is:

1. 2β-thiohydrazoazetidinones of structure:

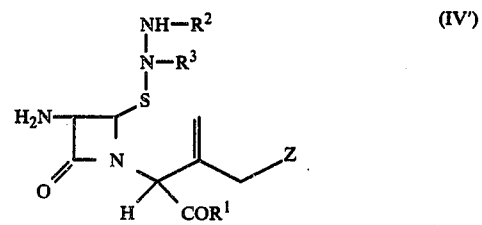

(IV′)

where R$^1$ is selected from the class consisting of hydroxyl, alkoxy having from 1 to 4 carbon atoms, trichloroethoxy, benzyloxy, p-methoxybenzyloxy, p-nitrobenzyloxy, benzhydryloxy, triphenylmethoxy, phenacyloxy, and p-halophenacyloxy;

z is selected from the class consisting of hydrogen, —O—alkyl, —Br, —I, —O—CO—CH$_3$; and R$^2$ and R$^3$ are equal or different and represent the radical —COOR$^4$ wherein R$_4$ is a lower alkyl having from 1 to 4 carbon atoms.

2. A compound selected from the class consisting of:
methyl-2β-thiohydrazodicarboxyethyl-α-isopropenyl-4-oxo-3β-amino-1-azetidine acetate;
2',2',2'-trichloroethyl-2β-thiohydrazodicarboxyethyl-α-isopropenyl-4-oxo-3β-amino-1-azetidine acetate and;
2',2',2'-trichloroethyl-2β-thiohydrazodicarboxyethyl-α-isopropenyl-4-oxo-3β-[N-(ter-butoxycarbonyl)-D-α-phenylglycinamide]-1-azetidine acetate.

3. Methyl-2β-thiohydrazodicarboxyethyl-α-isopropenyl-4-oxo-3β-amino-1-azetidine acetate.

4. 2',2',2'-trichloroethyl-2β-thiohydrazodicarboxyethyl-α-isopropenyl-4-oxo-3β-amino-1-azetidine acetate.

5. 2',2',2'-trichloroethyl-2β-thiohydrazodicarboxyethyl-α-isopropenyl-4-oxo-3β-[N-(ter-butoxycarbonyl)-D-α-phenylglycinamide]-1-azetidine acetate.

* * * * *

UNITED STATES PATENT AND TRADEMARK OFFICE
CERTIFICATE OF CORRECTION

PATENT NO. : 4,143,037
DATED : March 6, 1979
INVENTOR(S) : Maurizio FOGLIO et al Page 1 of 3

It is certified that error appears in the above-identified patent and that said Letters Patent are hereby corrected as shown below:

In the Abstract, formula (II') should read as follows:

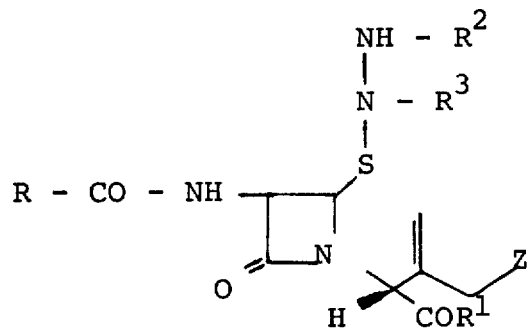

In the Abstract, formula (IV') should read as follows:

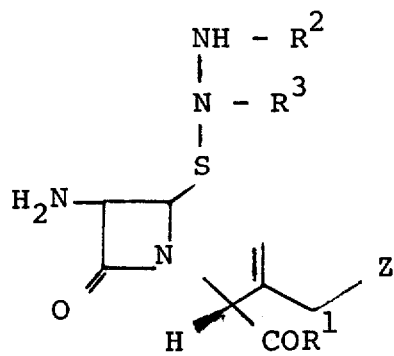

UNITED STATES PATENT AND TRADEMARK OFFICE
CERTIFICATE OF CORRECTION

PATENT NO. : 4,143,037

DATED : March 6, 1979

INVENTOR(S) : Maurizio FOGLIO et al

It is certified that error appears in the above—identified patent and that said Letters Patent are hereby corrected as shown below:

At column 3, formula (IV') should read as follows:

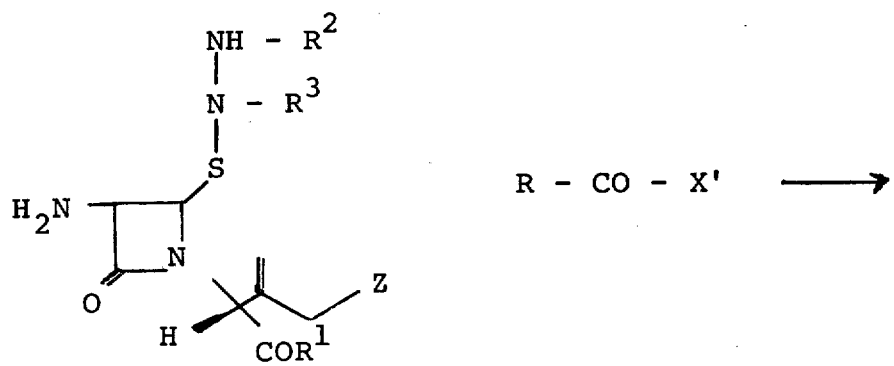

UNITED STATES PATENT AND TRADEMARK OFFICE
CERTIFICATE OF CORRECTION

PATENT NO. : 4,143,037
DATED : March 6, 1979
INVENTOR(S) : Maurizio FOGLIO et al It is certified that error appears in the above-identified patent and that said Letters Patent are hereby corrected as shown below:

At column 10, in Example 9, the first formula should read as follows:

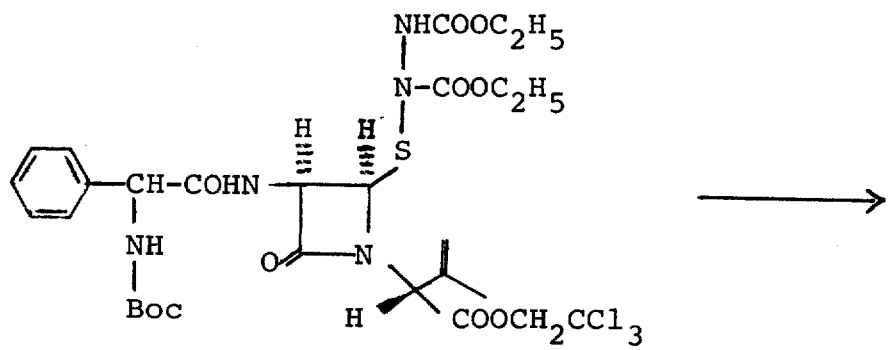

Signed and Sealed this

Twenty-fifth Day of September 1979

[SEAL]

Attest:

LUTRELLE F. PARKER
Attesting Officer    Acting Commissioner of Patents and Trademarks